US00PP08817P

United States Patent [19]

Fruehwirth

[11] Patent Number: Plant 8,817

[45] Date of Patent: Jul. 5, 1994

[54] POINSETTIA PLANT "490 PINK"

[75] Inventor: Franz Fruehwirth, Encinitas, Calif.

[73] Assignee: Paul Ecke Ranch, Inc., Encinitas, Calif.

[21] Appl. No.: 57,304

[22] Filed: May 4, 1993

[51] Int. Cl.[5] ..... A01H 5/00

[52] U.S. Cl. ..... Plt./86.3

[58] Field of Search ..... Plt. 86.3, 86.4

*Primary Examiner*—James R. Feyrer

*Attorney, Agent, or Firm*—Arnold, White & Durkee

[57] ABSTRACT

Poinsettia '490 PINK' is a new cultivar, distinguished by pink bracts and intense dark green foliage with self-branching characteristics. '490 PINK' is a color sport of the dark red bracted '490' (U.S. Plant Pat. No. 7,825) with the same early flowering response and cultural requirements. The new plant produces a very desirable branched flowering pot plant. The new plant is resistant to epinasty after being confined to shipping containers and recovers rapidly if the plant does become epinastic. The post-production foliage and bract retention is excellent even under low light intensities in the consumer's home.

1 Drawing Sheet

BACKGROUND OF THE NEW PLANT

This new poinsettia cultivar originated as an induced pink bracted sport of 490 (U.S. Plant Pat. No. 7,825) in my greenhouse in Encinitas, Calif. It was induced by irradiation of 100 vegetative plants of '490' with 4000 rads of radiation, randomly applied to the whole plant under conditions which were not lethal to the plant. Of the 100 plants irradiated, one plant exhibited pink bracts. The mutant plant exhibited early flowering, self branching, pink flower bracts and dark green foliage; traits which help distinguish it from other poinsettia cultivars, and seem to make it a desirable plant for commercial greenhouse production.

'490 Pink' differs from the parent plant '490' in its distinctly different pink bract color. In contrast, parent '490' exhibits dark red bracts. Otherwise, the two plants are similar in size, height, leaf shape, and other characteristics.

After selection, '490 PINK' was vegetatively reproduced from stem cuttings for test purposes in Encinitas, Calif. By subjecting clones of this plant to successive generations of vegetative propagation, it was demonstrated that the distinctive characteristics of '490 PINK' held true from generation to generation.

DESCRIPTION OF THE PHOTOGRAPH

Poinsettia '490 PINK' is illustrated in the accompanying color photograph. The upper photo is a side view of 3 single stem plants per pot in full flower. Evidence of self branching can be seen in the flowering axillary branches beneath the upper canopy of bracts. The lower photo is a top view of the same plants showing flower and bract formation.

DESCRIPTION OF THE PLANT

The following is a detailed description of this new poinsettia as observed in Encinitas, Calif., U.S.A. during December 1992. Observations were recorded from flowering plants, grown as 3 single stem plants per pot. The pot was 14 cm. in diameter and 11 cm. in height. Color designations are compared to the 1986 edition of R.H.S. Colour Chart, first published in 1966 by The Royal Horticultural Society, London, England.

THE PLANT

Origin: Sport of '490' (U.S. Plant Pat. No. 7,825), induced through irradiation of vegetative plants with 4,000 rads of radiation.

Classification:

*Botanic.*—*Euphorbia pulcherrima* Willd.

*Common name.*—Poinsettia.

*Cultivar name.*—490 Pink.

Form: Shrub.

Height: Short.

Growth habit: As a single stemmed plant, upright and short with self-branching side shoots. The application of a chemical growth retardant may not be needed to restrict height for commercial pot plant production. I observed 3 unpinched plants in a pot with an overall height of 34 cm. and an overall width of 46 cm. The bract diameter of individual flowers was 32 cm.

Branching: Axillary branches will develop and terminate in a flower without pinching. However, it is usually desirable to pinch '490 Pink' and remove all terminal dominance. Then, all axillary branches will develop uniformly and at a faster rate.

Growth rate: Rooting of stem cuttings occurs in 12–18 days under intermittent mist.

Flowering: The plant will flower in about eight weeks under continuous long night conditions and night temperatures of about 16–18 degrees C. Like its parent ('490'), '490 Pink' will be in full bloom in mid-November in the northern hemisphere under natural daylength conditions. '490 Pink' flowers earlier than most known poinsettias because flower induction seems to occur in mid-September, about 10 days earlier than normal.

Foliage: At flowering, plants were observed with about 15 uniformly dark green leaves, one leaf per node. The leaves were of medium size, leaf blades typically being about 11–13 cm. long and about 8 cm. wide with leaf petioles about 6 cm. long. Between the green leaves and the true flower bracts were 4 transitional bracts from the uppermost nodes on each stem. These leaf/bracts were green but changed to pink as the flowers matured. At maturity, one or two of these leaf/bracts were neither completely green nor completely pink as seen in the photograph.

*Leaf shape.*—Typical leaves are generally ovate with obtuse bases and acuminate tips. Leaf margins are entire or slightly lobed with 1 or 2 indentations on each side of the leaf blade.

*Color.*—Upper side — Dark green, darker than RHS 139A. Under side — Green, lighter than but near RHS 147A.

Bracts: Generally there were 15–18 pink bracts of various sizes subtending the cyathia. The primary bracts have blades typically 15–17 cm. long and 11–12 cm. wide with petioles about 5 cm. long.

*Shape.*—Primary bracts are ovate with acute bases and acuminate tips and weakly lobed with 1 small indentation on either side of the bract. Secondary bracts are elliptic and have entire margins.

*Color.*—Upper side — Pink. The smaller secondary bracts are bright pink near RHS 53C. The older primary bracts are faded to near RHS 54A, however, the bract veins retain the deeper pink (RHS 53C) on the upper surface making the venation more prominent on the larger bracts. Under side — Pink. Smaller secondary bracts near RHS 53D. Larger bracts nearer RHS 54C.

Flowers:

*Cynthia.*—Generally, 16 cyathia (flowers) were present when the plant was in full bloom. Each cyathium was about 7 mm long and 6 mm wide, green in color, and fringed with red at the distal end. A yellow nectar cup protrudes from the side of each cyanthium. The flower pedicel is also green and about 4 mm in length. The stamens protruding from the cyathia are red. The anthers are bifurcate with copious yellow pollen. Cyathia last for approximately three weeks after the plant is in full bloom.

*Nectar exudate.*—Abundant.

*Seed formation.*—Self-incompatible.

*Fertility.*—Not observed.

Post production '490 PINK' is resistant to epinasty after being confined to shipping containers and recovers rapidly if the plant does become epinastic. The foliage and bract retention is excellent even under low light intensities in the consumer's home.

What is claimed is:

1. A new and distinct Poinsettia cultivar, substantially as herein shown and described, distinguished by its intense dark green foliage, pink bracts and epinasty resistance.

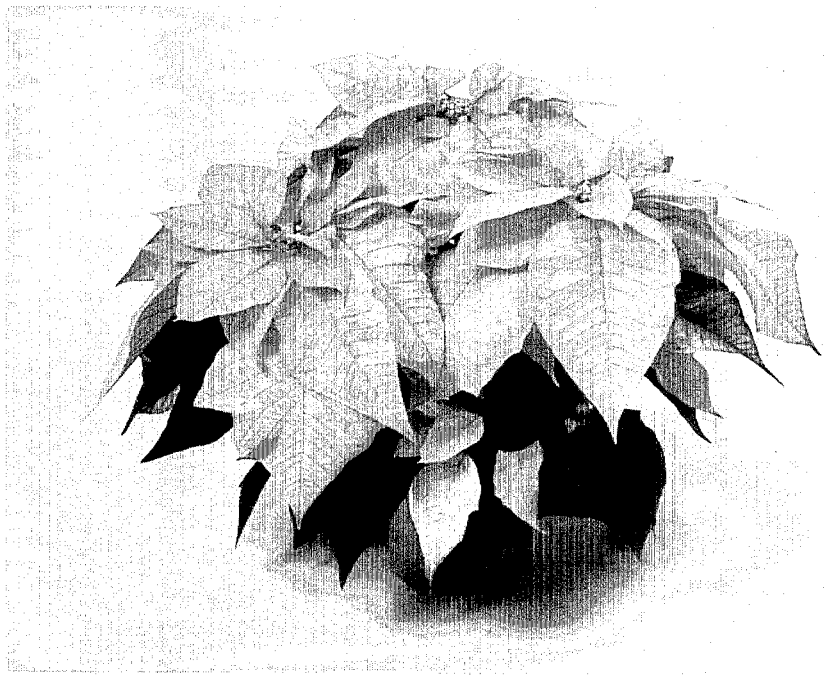
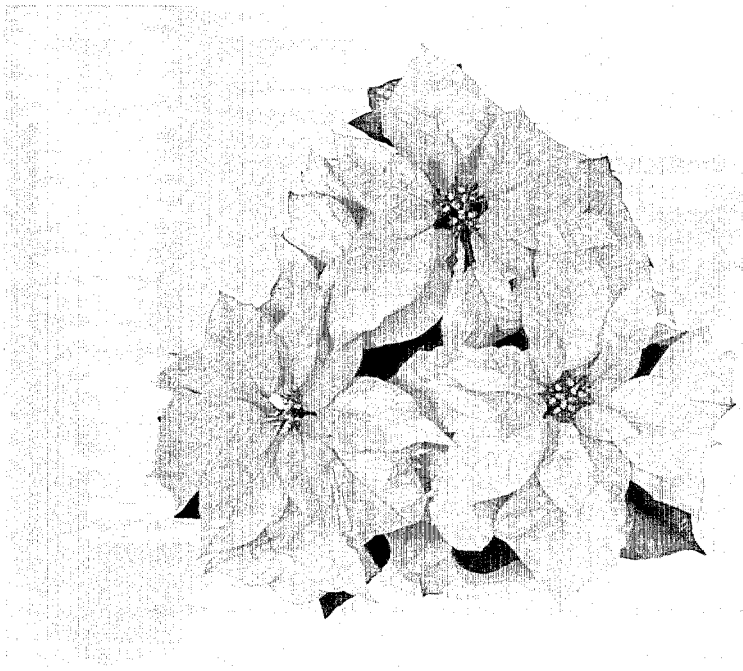

* * * * *